United States Patent [19]
Staub

[11] Patent Number: 5,615,962
[45] Date of Patent: Apr. 1, 1997

[54] LOTION APPLICATOR

[76] Inventor: Nancy K. Staub, 1435 Maryland Ave., Woodbridge, Va. 22191

[21] Appl. No.: 443,386

[22] Filed: May 17, 1995

Related U.S. Application Data

[63] Continuation of Ser. No. 111,058, Aug. 24, 1993, abandoned.

[51] Int. Cl.$^6$ .............................. B05C 11/02; A45D 40/06
[52] U.S. Cl. .......................... 401/173; 401/176; 401/196; 99/507; 100/125; 100/213
[58] Field of Search .................................. 241/168, 169, 241/89.2, 89.3; 222/390, 174; 604/310, 311, 289; 401/28, 196, 173, 176, 6; 99/507, 508; 100/125, 238, 213, 130; 210/470, 471; 209/417; 132/320

[56] References Cited

U.S. PATENT DOCUMENTS

| | | | |
|---|---|---|---|
| 52,928 | 2/1866 | Fogerty | 100/213 |
| 104,159 | 6/1870 | Jensen | 100/213 |
| 414,499 | 11/1899 | Cullinane | 100/213 X |
| 543,200 | 7/1895 | Verpillier et al. | 401/172 |
| 581,628 | 4/1897 | Snyder | 241/89.3 |
| 850,357 | 4/1907 | Doyle | 401/176 X |
| 1,501,089 | 7/1924 | Andrews | 401/28 |
| 1,586,371 | 5/1926 | Lape | 401/173 |
| 1,712,802 | 5/1929 | Willis | 241/168 X |
| 1,839,742 | 1/1932 | Davis | 401/173 X |
| 1,885,997 | 11/1932 | Durham | 401/173 |
| 2,018,932 | 10/1935 | Thorne | 99/507 X |
| 2,085,446 | 6/1937 | Philippe | 401/176 X |
| 2,818,797 | 1/1958 | Ballor | 100/289 X |
| 4,348,950 | 9/1982 | Harris | 100/125 X |
| 4,981,041 | 1/1991 | Merkle | 401/176 X |

FOREIGN PATENT DOCUMENTS

| | | | |
|---|---|---|---|
| 1274216 | 9/1990 | Canada | 401/196 |
| 424869 | 5/1911 | France | 100/125 |
| 2623983 | 6/1989 | France | 401/6 |
| 2625743 | 12/1977 | Germany | 132/320 |
| 17943 | 2/1905 | Sweden | 401/173 |
| 26423 | 12/1904 | United Kingdom | 401/173 |
| 430894 | 1/1935 | United Kingdom | 210/471 |

*Primary Examiner*—Danton D. DeMille
*Attorney, Agent, or Firm*—Peter A. Borsari

[57] ABSTRACT

A device for applying lotions, creams and similar substances to any part of the body, particularly to the back and other difficult-to-reach areas is provided. The applicating device comprises three basic components: a one-piece frame having an elongated handle portion at one end and a reservoir retaining means at the distal end thereof, a pressure applying lid having top, central and bottom portions and a removable flexible reservoir having a porous, permeable or perforated applicator surface. The pressure applying lid and retaining means are configured to interact thereby advancing the lotion through the applicator surface. The applicator surface has a convex curvature which is substantially identical to the curvature of the bottom portion of the pressure applying lid, thereby minimizing waste of the lotion.

1 Claim, 1 Drawing Sheet

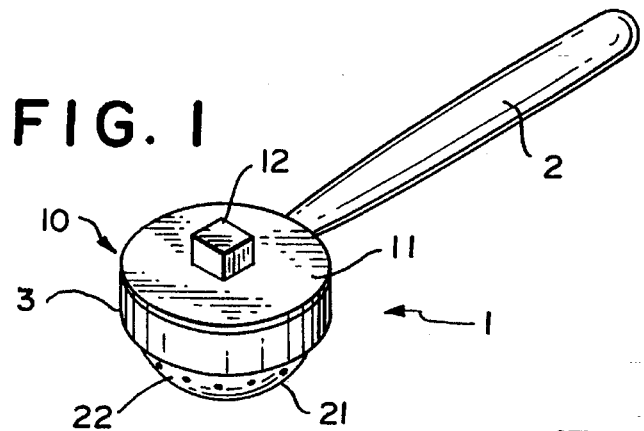
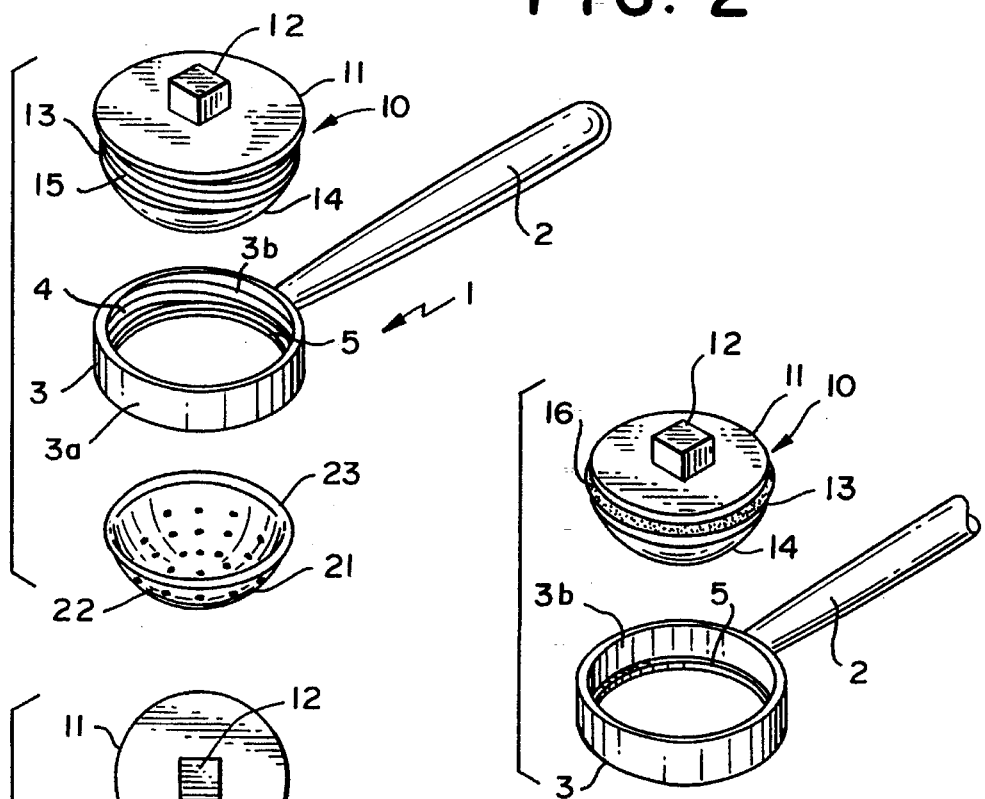
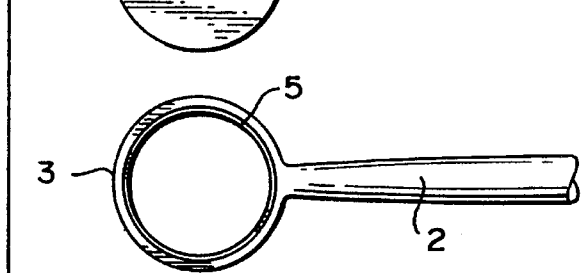
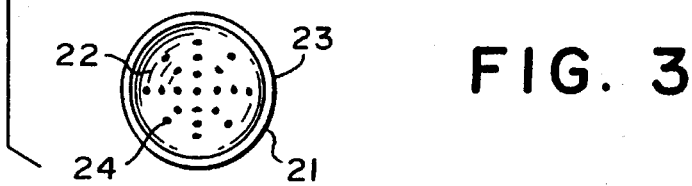

LOTION APPLICATOR

This application is a continuation of application Ser. No. 08/111,058, filed Aug. 24, 1993, now abandoned.

FIELD OF INVENTION

The present invention relates to an applicator comprising three fundamental elements, by means of which lotions, creams, gels, soft pastes and similar materials may be simply and easily applied to any part of the body, and particularly to the back and other remote areas.

BACKGROUND OF THE INVENTION

It is occasionally necessary for an individual to apply lotions, creams and similar materials, particularly medicated substances, to the back and other difficult-to-reach areas of the body. Such application, especially to the back, is sometimes a cumbersome, if not impossible, task and usually requires the assistance of another individual. However, in this day, with an ever-increasing singles population and a rise in the number of elderly and handicapped people living alone, there is a need for a device with which this task can be simply and easily accomplished.

The prior art is replete with applicating and dispensing devices for reaching remote areas of the body. In most instances, these devices comprise a handle and an applicating means. U.S. Pat. No. 2,829,393 to Turcotte provides a simple applicating means in the form of a porous pad made from foam rubber, foam plastic or other substantially elastic material, which is fitted over a reservoir. This long-handled sponge has inherent disadvantages, the most significant of which include (1) the waste of lotion or other substance which has been absorbed by the sponge material, (2) regular drying out and stiffening of the sponge material, thereby causing a loss of elasticity, and (3) difficulty in cleaning the sponge for re-use.

Also known are the more complicated applicator devices which comprise a number of components in either or both the handle and applicating means. Two fundamental problems exist with such devices: the numerous parts (1) add to the cost of manufacture and (2) increase the likelihood that one or more parts will fail. U.S. Pat. No. 4,927,283 to Fitjer relates to a device for the application of a liquid or pasty material wherein the applicating means is detachably mounted on a handle and comprises a sealed chamber containing a liquid or pasty material. The handle includes a manually operated release which breaks or punctures the seal of said chamber, thereby releasing the material. A major disadvantage of the Fitjer device is that the sealed chamber containing the liquid or pasty material is manufactured as a separate item, thereby severely limiting the consumer's choice of products. In U.S. Pat. No. 4,483,636 to Meyer, a suntan lotion applicator is disclosed, said applicator comprising a handle portion which also serves as a supply reservoir, and a dispensing head at the distal end thereof. The dispensing head comprises several parts including a flat application surface which is covered by a compressible porous pad.

Other devices employ a piston-type element to force a lotion or other material from a supply reservoir to an applicating head. U.S. Pat. No. 4,269,527 to Lipfert et al. provides an applicator for pulverized substances wherein said pulverized substances may be forced through perforations in a permeable membrane by a plunger which is advanced by a screwing action. U.S. Pat. No. 4,865,231 to Wiercinski discloses a swivel-up type dispensing package having a feed screw and nut associated with an elevator-like system for advancing towards an applicating surface. In U.S. Pat. No. 850,357 to Doyle, an inflexible rubber head is lubricated with a lotion by means of a piston-type plunger. In U.S. Pat. No. 5,059,050 to Guglielmo, a flat plate piston is utilized to apply pressure from the reservoir to a dispensing nozzle in hair treatment applications.

Still other types of applicators exist for a wide variety of products, including lotions, inks and shoe pastes, and have different applicating means, such as brushes or combs, as shown in U.S. Pat. Nos. 797,089 to Trimble, 543,200 to Verpiller et al., 1,465,220 to Huether, 4,143,982 to Cox, 4,090,422 to Donley and 2,590,417 to Jardines.

All of the prior art applicator devices have several limitations or disadvantages associated therewith, including (a) the waste of lotion, (b) difficulty in use and cleaning of the various elements and (c) too many components, which increases manufacturing costs and the probability that one or more element will fail.

Despite the teachings of the prior art, a need still exists for an uncomplicated applicating device which has a simplicity of construction, is inexpensive to manufacture, is simple and easy to use and clean, and which controls the amount of lotion or similar material to be applied.

SUMMARY OF THE INVENTION

Accordingly, it is an object of the present invention to provide an applicating device which is of simple construction and comprises few parts.

It is another object of the present invention to provide an applicating device wherein lotions, creams and similar materials may be simply and easily applied to any part of the body by one individual.

It is still another object of the present invention to provide an applicating device which has a removable and replaceable flexible applicating means.

It is a further object of the present invention to provide an applicating device which is easy to clean.

It is an additional object of the present invention to provide an applicating device which controls the amount of lotion, cream or the like to be applied to the body.

It is yet another object of the present invention to provide an applicating device which is inexpensive to manufacture.

Additional objects, advantages and novel features of the invention will be set forth in part in the description which follows, and in part will become apparent to those skilled in the art upon examination of the following specification or may be learned by practice of this invention.

These and other objects of the invention, as embodied and broadly described herein, are achieved by providing an improved device for applying lotions, creams, and similar substances to any part of the body, said device comprising (1) a one-piece elongated frame having a handle portion at one end and a reservoir retaining means at the distal end thereof, (2) a pressure applying lid and (3) a removable flexible reservoir.

BRIEF DESCRIPTION OF THE DRAWINGS

The present invention will be better understood with reference to the appended drawing sheets, wherein:

FIG. 1 shows a side view of the applicating device of the present invention which is assembled and ready for use.

FIG. 2 shows an exploded side view of each of the three individual components of the applicating device.

FIG. 3 shows an exploded top view of each of the three individual components of the applicating device.

FIG. 4 shows an exploded side view of an alternative embodiment of the applicating device.

DETAILED DESCRIPTION

The present invention relates to an improved device for applying lotions, creams and similar substances to any part of the body, particularly to the back and other difficult-to-reach areas. As shown in FIG. 1, the lotion applicator, sometimes hereinafter referred to as an applicating device, comprises three basic components: (1) a one-piece frame 1 having an elongated handle portion 2 at one end and a reservoir retaining means 3 at the distal end thereof, (2) a pressure applying lid 10 having a top portion 12, a central portion 13 and a bottom portion 14 and (3) a removable flexible reservoir 21. The proximal end of handle portion 2 may be smooth or may be configured to enhance a manual grip. The one-piece frame may be composed of any material and is preferably molded from any suitable plastic, such as polyethylene, polypropylene, polyvinylchloride and the like.

The reservoir retaining means 3, located at the distal end of said one-piece frame 1, comprises an exterior surface 3a and an interior surface 3b. The reservoir retaining means 3 serves to position both the lid and reservoir. The retaining means 3 comprises a rim 5 disposed on interior surface 3b, as shown in FIG. 2. The interior surface 3b may be substantially smooth, notched, grooved, threaded or otherwise configured. Preferably, as shown in FIG. 2, the reservoir retaining means 3 is fabricated in the form of a circular ring or collar, wherein the interior surface is provided with grooves 4.

The pressure applying lid 10 comprises a top portion 11 upon which a knob-like handle 12 is located. Preferably, the lid is molded from the same plastic material as the one-piece frame 1; however, any suitable material may be used in making the pressure applying lid. The outer periphery of central portion 13 is fashioned in such a manner to correspond with the interior surface 3b of retaining means 3 and may be, for example, smooth, notched or threaded. The bottom portion 14 is preferably in the form of a convex dome, as shown in FIG. 2.

The reservoir 21 comprises an annular flange 23 for positioning and retaining the reservoir within the retaining ring 3 and a porous, permeable or perforated applicator surface 22. The applicator surface 22 has one or more perforations 24 disposed therein which enables the lotion or other substance in the reservoir to be delivered from said reservoir to the body. The size, number and distribution of perforations 24 may be varied as long as the substance in the reservoir can be effectively applied to the body surface. Applicator surface 22 can be of any material suitable for contact with a body surface, such as a plastic screen, mesh or permeable plastic. Preferably, the applicator surface is composed of a soft, flexible plastic film material.

The relative sizes of the pressure applying lid 10 and the retaining ring 3 are fashioned in such a manner to enable the pressure applying lid 10 to mate, join or otherwise fit inside and interact with the retaining ring 3. Accordingly, the periphery surface of central portion 13 should correspond and complement the interior surface 3b of said retaining ring. In this manner, downward movement of the pressure applying lid 10 imparts a piston or plunger-like function within the ring, whereby lotion is urged from the reservoir for application to the body. In the preferred embodiment shown in FIG. 2, the outer periphery of central portion 13 is threaded 15 in order to engage grooves 4 on interior surface 3b. In this manner, as the lid 11 is rotated clockwise or counter clockwise in the retaining ring 3, the lid will be axially lowered or raised toward or away from the reservoir, respectively.

The curvature of bottom portion 14 is configured to correspond to the curvature of applicator surface 22, thereby providing an intimate fit with the applicator surface upon contact thereof. In the preferred embodiment shown in FIG. 2, the applicator surface 22 has a convex curvature which is substantially identical to the curvature of bottom portion 14.

In use, once the lotion has been placed in the reservoir 21, the pressure applying lid 10 is positioned on top of reservoir retaining means 3. Upon rotation of the knob-like handle 12, threads 15 engage grooves 4, thereby advancing the bottom portion 14 downwardly toward the applicator surface 22. This action urges the lotion through perforations 24 in the applicator surface. Further rotation of the knob-like handle 12 controls the amount of lotion dispensed through the perforations. Since the curvature of bottom portion 14 is substantially identical to the curvature of the applicator surface 22, continued rotation of knob 12 will result in the complete discharge of the lotion contained in the reservoir. In this manner, there is minimal waste of the lotion. Once all the lotion has been discharged, the lid 10 is detached by rotation in the opposite direction and reservoir 21 is removed from the retaining ring. Thereafter, the lid and reservoir can be washed or wiped in order to remove any residual lotion.

FIG. 4 depicts an alternative embodiment, wherein the interior surface 3b of the retaining ring 3 is substantially smooth, with the exception of annular rim 5. About the outer periphery of central portion 13 of lid 10, a rubber gasket or similar member 16 is secured. In this manner, a friction fit is provided when lid 10 is seated on top of retaining ring 3. Downward movement of the lid in the direction of the reservoir 21 advances the bottom portion into contact with lotion in the reservoir, thereby urging the lotion through the perforated applicator surface.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. An applicator device for dispensing lotions, creams, gels, soft pastes and similar body-treating substances consisting of:
   (1) a frame member having proximal and distal ends, said proximal end defining an elongated handle and said distal end defining an annular ring having (a) an interior surface configured with grooves and (b) a rim disposed on its interior surface for supporting and retaining a removable convex reservoir;
   (2) a pressure applying lid having (a) a top portion, (b) a central portion having an outer periphery configured with threads, said threads configured to matingly engage said grooves of said interior surface of said annular ring, and (c) a bottom portion in the form of a convex dome; and
   (3) a removable convex reservoir adapted for receiving, retaining and dispensing a body treating substance being configured to complement the contour of said convex dome and having (a) an applicating surface having perforations and (b) an annular flange adapted for cooperating engagement with said rim of said annular ring for fixedly but removably supporting said reservoir on said frame member;

whereby mating engagement of said threads and grooves by a rotation of said pressure applying lid will cause a movement of said pressure applying lid, such that rotation in a first direction moves said pressure applying lid toward said convex reservoir and rotation in a second and opposite direction moves said pressure applying lid away from said convex reservoir wherein rotation in said first direction generates a pressure upon a body-treating substance retained between said bottom portion of said pressure applying lid and said removable convex reservoir, said pressure being functional to motivate said body-treating substance through said perforations in said applicating surface.

* * * * *